United States Patent [19]

Jacobs, III et al.

[11] Patent Number: 4,897,435

[45] Date of Patent: * Jan. 30, 1990

[54] WATER BASED HYDROXYALKYL CARBAMATE-CONTAINING RESINS AND METHOD OF MAKING THE SAME

[75] Inventors: William Jacobs, III, Bridgeport; Werner J. Blank, Wilton, both of Conn.

[73] Assignee: American Cyanamid Company, Stamford, Conn.

[*] Notice: The portion of the term of this patent subsequent to Nov. 27, 2001 has been disclaimed.

[21] Appl. No.: 581,009

[22] Filed: Feb. 17, 1984

[51] Int. Cl.$^4$ .............................................. C08G 59/14
[52] U.S. Cl. .................................... 523/414; 525/504; 525/523; 528/111; 528/99; 528/361; 528/369
[58] Field of Search ................ 525/504, 523; 528/45, 528/73, 111, 361, 99, 369; 523/414

[56] References Cited

U.S. PATENT DOCUMENTS

| | | |
|---|---|---|
| 3,922,253 | 11/1975 | Jerabek et al. .................... 528/45 |
| 3,984,299 | 10/1976 | Jerabek ........................ 523/415 X |
| 4,017,438 | 4/1977 | Jerabek et al. .................... 523/420 |
| 4,031,050 | 6/1977 | Jerabek ........................ 528/45 X |
| 4,101,486 | 7/1978 | Bosso et al. ....................... 528/45 |
| 4,260,716 | 4/1981 | Christenson et al. .............. 528/45 |
| 4,435,559 | 3/1984 | Valko ................................. 528/73 |
| 4,484,994 | 11/1984 | Jacobs et al. . | |
| 4,528,363 | 7/1985 | Tominaga ........................ 528/370 |

Primary Examiner—Earl Nielsen
Attorney, Agent, or Firm—Roger S. Benjamin

[57] ABSTRACT

A hydrophilic, substantially epoxy-free self-cross-linkable polymer contains hydroxyalkyl carbamate groups and one or more tertiary amine groups. The polymer suitably is made by reacting an epoxy resin having an average epoxy equivalent weight of from about 100 to about 700 with one or more amines having at least one secondary amine group and at least one hydroxyalkyl carbamate group or precursor thereof. A coating composition comprises an aqueous medium containing the polymer and, optionally, a cross-linking catalyst. A low temperature-curable coating is attained by utilization of the polymer with a suitable quaternary or ternary compound catalyst.

31 Claims, No Drawings

WATER BASED HYDROXYALKYL CARBAMATE-CONTAINING RESINS AND METHOD OF MAKING THE SAME

BACKGROUND OF THE INVENTION

The present invention concerns water-based self-cross-linkable resins for use in the application of coatings to substrates, a method of preparing such resins and coating compositions containing the resins. The present invention also concerns a method for making low temperature cured, cross-linked coatings from the self-cross-linkable material of the invention.

Coating systems based on organic solvent-based materials, such as isocyanate systems, are available which provide high performance, urethane cross-linked coatings but engender environmental and fire hazards because of the use of volatile or toxic organic solvents. Commercially available isocyanate compounds typically are toxic and highly reactive, requiring the taking of suitable precautions in handling and storing the same. Aqueous solutions or dispersions of polyurethanes for coatings are known, but these known systems usually require high curing temperatures on the order of 350° to 600° F. (176° to 315° C.) in order to obtain cross-linking through the urethane groups. Although other low temperature-, or even room temperature-curable aqueous solutions or dispersions of isocyanate-free polyurethanes are available, such coatings do not cross-link through urethane groups and therefore are not likely to meet the performance standards attainable by urethane cross-linked coatings. Most aqueous dispersions of polyurethanes are usually attained by the addition of acids to form cationic dispersions or by the addition of bases to form anionic dispersions, or by the addition of surfactants, all of which additives can adversely affect the properties of the cured film obtained thereby. For example, the aqueous cationic-, anionic-, or surfactant-dispersed isocyanate-based polyurethanes often suffer from a lack of stability upon aging. If there are -NCO groups present, a reaction between water and the isocyanate will usually take place within about three to twenty hours at room temperature. Thus, isocyanate-based polyelectrolytes which are fully solule in water either readily hydrolyze in water of, after removal of water, become brittle and hygroscopic. Because of these drawbacks occasioned by the high ion group content of such materials, they are not of significant practical importance in the field of coatings and plastics generally.

One class of non-ionic aqueous solutions of polyurethanes is based upon the incorporation of polyester-glycol or polyether-glycol segments. However, the polyester-glycol types are sensitive to hydrolytic degradation while the water solubility of the polyether-glycol based resins is isocyanate-dependent. Moreover, both types tendto yield cured films with excessive sensitivity to water, i.e., films which are subject to swelling, turbidity (turning white), softening, and variable adhesion upon exposure to water.

Numerous literature references exist showing the reactions of primary and secondary amines with, for example, propylene carbonate to yield corresponding hydroxypropyl carbamates (*Compt. rend.* 1142, 1954). The literature also shows that bishydroxyalkyl carbamates derived from corresponding diamines have been further self-condensed, or transesterified with other diols, to produce linear thermoplastic polyurethanes. For example, see the article "The Preparation of Polymeric and Cyclic Urethans and Ureas from Ethylene Carbonate and Amines" by Elizabeth Dyer and Harvey Scott, *J.A.C.S.* (1956) pp. 672–675. See also the report "Polyurethane elastomers obtained without the use of diisocyanates" by L. Ya. Rappoport, G. N. Petrov, I.I. Trostyanskaya and O. P. Gavrilova in *International Polymer Science and Technology*, 8, No. 1, 1981 and an article by Richard D. Cowell entitled: "Thermoplastic Polyurethane Elastomers: Chemistry Properties and Processing for the 80's" in the *Journal of Elastomers and Plastics*, Vol. 14, (October, 1982) pages 195–203.

SUMMARY OF THE INVENTION

It has now been found that a hydrophilic polymer can be prepared in which hydroxyalkyl carbamate groups are incorporated, preferably by reaction of amines and-/or polyamines with cyclic carbonates to provide a hydroxyalkyl carbamate group-containing secondary amine which is reacted with a suitable epoxy resin or the like. The resultant hydrophilic polymers are well suited to the production of high performance coatings and do not rely on the presence of polyester or polyether-glycol segments for water solubility/reducibility, are non-ionic, have indefinite shelf life stability and, since the hydrophilic groups are lost during cure, the coatings are not sensitive to water.

The present invention broadly provides a novel composition of matter attained by the incorporation of hydroxyalkyl carbamate groups into a thermosettable amine resin, the hydroxyalkyl carbamate groups serving both as cross-linking sites and as water-solubilizing sites on materials which are otherwise water insoluble.

In accordance with the present invention, there is provided a hydrophilic, substantially epoxy-free self-cross-linkable polymer which contains hydroxyalkyl carbamate groups and one or more tertiary amine groups. Preferably, the polymer is obtained as the reaction product of (a) an epoxy resin having an average epoxy equivalent weight of from about 100 to about 700, preferably from about 100 to about 300, and (b) one or more amines having at least one secondary amine group and at least one hydroxyalkyl carbamate group or precursor thereof.

Preferred aspects of the invention may include one or more of the following features: the epoxy resin may be selected from the group consisting of (i) the reaction product of epichlorohydrin and a polyhydric phenol, and (ii) the reaction product of epichlorohydrin and a condensation product of phenol with acetone and formaldehyde; and the polymer may contain from about 3.5 to about 5.7 milliequivalents ("meq"), preferably from about 4.2 to about 5.4 meq, hydroxyalkyl carbamate per gram of resin solids.

In another aspect of the invention, there is provided a method of preparing a hydrophilic self-cross-linkable polymer, which method comprises reacting (a) an epoxide having an average epoxy equivalent weight of from about 100 to about 700, preferably from about 100 to about 300, with (b) an amine containing at least one secondary amine group and at least one group selected from the class consisting of hydrolyzable blocked primary amine groups and hydroxyalkyl carbamate groups, to form a substantially epoxy-free material and, when said blocked primary amine groups are present, hydrolyzing the same to unblock said primary amine groups and then reacting a cyclic carbonate with said primary amine groups to form said hydroxyalkyl carbamate groups; the reactants (a) and (b) being selected to form said polymer with from about 3.5 to about 5.7, preferably from about 4.2 to about 5.4, meq hydroxyalkyl carbamate per gram of resin solids.

One aspect of the invention relates to a coating composition comprising a polymer as described above in aqueous medium. The coating composition may further include a cross-linking catalyst and a cross-linked coating may be prepared by heating the deposited coating at a temperature and for a time sufficient to cure it.

Another aspect of the invention relates to a coating composition including, e.g., a ternary or quaternary compound cross-linking catalyst, the coating obtained therefrom being curable at relatively low temperatures, e.g., from about 200° to about 250° F. (about 93° to 121° C.), and within about one hour, e.g., about 20 to about 30 minutes.

Other aspects of the invention include utilizing epoxides and amines of the general and specific formulas indicated below to form the polymer of the invention. As used herein and in the claims, "epoxy equivalent weight" has its usual meaning of the molecular weight of the epoxide divided by the number of epoxy groups on the molecule, i.e., for a monoepoxide, the equivalent weight equals the molecular weight.

DETAILED DESCRIPTION OF THE PREFERRED EMBODIMENTS

Cyclic carbonates such as ethylene or propylene carbonate react with amines to form hydroxyalkyl carbamates, according to the following typical example, in which $R_a$ is assumed to be hydrogen:

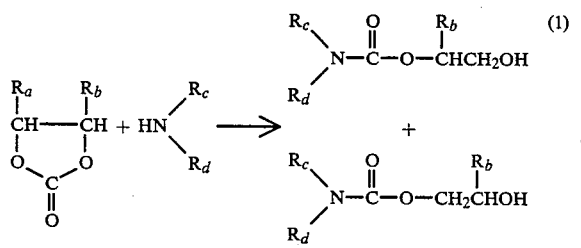
(1)

where $R_b$ is hydrogen for ethylene carbonate and methyl for propylene carbonate. The reaction may be run with or without solvent and, if so desired, protic solvents such as water or alcohols may be used. When either $R_c$ or $R_d$ is hydrogen, as in an unhindered primary amine, the reaction takes place at room or slightly elevated temperatures whereas secondary or hindered primary amines usually require heating and/or the use of catalysts for significant reaction to occur. This difference in reactivity allows for the preparation of a wide variety of hydroxyalkyl carbamates containing any number of hindered primary or secondary amine groups. For example, the polyamine below will only react at primary amine sites at room or slightly elevated temperatures even with excess cyclic carbonate.

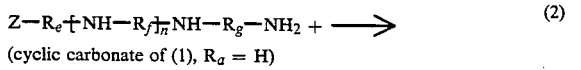
(2)

(cyclic carbonate of (1), $R_a$ = H)

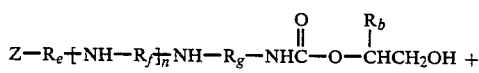

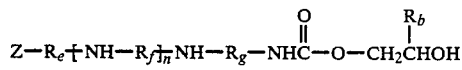

Hydroxyalkyl carbamate amines as illustrated in equations (1) and (2) above are useful in this invention if they impart water solubility/reducibility to normally water insoluble epoxy resins after the resins have been reacted with the hydroxyalkyl carbamate-containing amines. Useful di- or polyamines for the formation of hydroxyalkyl carbamate amines as illustrated above are those where n is from zero to about 5, $R_e$, $R_f$, and $R_g$ are straight chained or branched hydrocarbon fragments having one to about six carbon atoms, and where $R_e$, $R_f$ and $R_g$ may also contain an ether group.

The Z group may be selected from: hydrogen, hydroxyl, or an alkoxy of from 1 to 20 carbon atoms, or a secondary amine of from 1 to 20 carbon atoms, or a primary $-NH_2$ group. In the latter case, the primary amine group Z may be converted to a hydroxyalkyl carbamate group if enough (or excess) cyclic carbonate is utilized to form the hydroxyalkyl carbamate amine (or polyamine) compound.

The resulting hydroxyalkyl carbamate-containing amine is reacted with a water-insoluble, epoxide-containing "backbone" compound, which reaction may be generally represented as

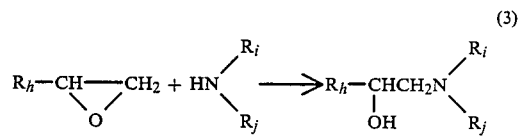
(3)

where $R_h$ is a fragment of an epoxy-containing resin and $R_i$ and $R_j$ are fragments of the above-described hydroxyalkyl carbamate-containing amine or polyamine compounds. The reaction usually occurs at room or slightly elevated temperatures and is often exothermic. The reaction may be performed without a solvent, otherwise aprotic or alcohol solvents may be used. Numerous types of mono or polyfunctional epoxides may be used, such as acyclic aliphatic, cyclic aliphatic, aromatic, heterocyclic, or oxygen or tertiary amine group-containing epoxides. For example, a typical polymer in accordance with the invention may have the formula:

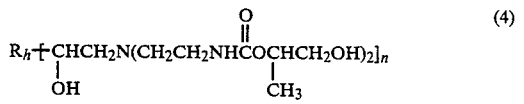
(4)

The resultant polymer, upon heating and, optionally, in the presence of a suitable cross-linking catalyst, will cross-link through one or more mechanisms, as follows: by cross-linking through backbone hydroxyl groups

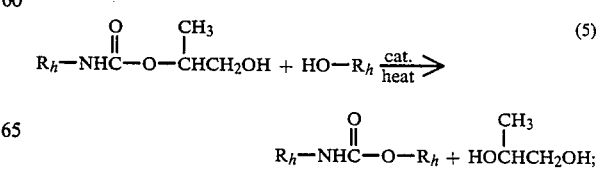
(5)

by cross-linking through self-condensation

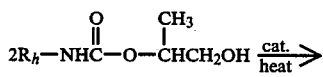

(6)

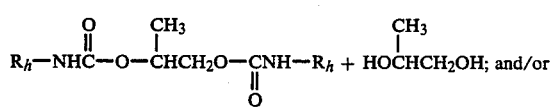

by cross-linking through backbone amine groups

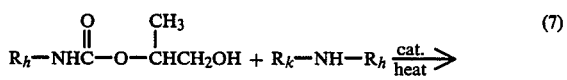

(7)

wherein $R_k$ is hydrogen or a fragment of the backbone polymer. It should be noted that in all of the cross-linking reactions (5), (6) and (7), the water solubilizing hydroxyalkyl portion of the carbamate group is lost as a glycol. The cross-linked films therefore not only develop good mechanical properties and solvent resistance during cure but also regain the inherent water resistance of the original epoxides. This conversion of the hydrophilic polymer to a water-resistant cured product is a significant advantage of the invention.

Generally, the multi-functional amines utilized in the invention contain at least one secondary amine group which is hindered with respect to reacting with the cyclic carbonate and at least one primary amine group. As used herein and in the claims, (a) "multi-functional amine" means an amine containing at least one primary amine group (which may be a blocked primary amine group as described below) and at least one hindered secondary amine group; and (b) "hindered secondary amine group" means a secondary amine group which is inhibited, sterically, electronically or otherwise, with respect to reacting with the cyclic carbonate under conditions at which the primary amine group will react. The secondary amine groups which are sterically or otherwise inhibited from reacting with a cyclic carbonate thus survive formation of the carbamate and are reactive with the epoxy groups on the polymer.

The above definition of "multi-functional amine" is intended to include blocked primary amine groups, such as ketimine groups, which can be unblocked to form the primary amine group. As described in more detail below, the multi-functional amine can optionally be reacted with the epoxide prior to formation of the hydroxyalkyl carbamate groups by having the primary amine groups in the form of blocked primary amines, e.g., ketimine groups. After reaction with the epoxide, the ketimine groups may be hydrolyzed to primary amine groups and then reacted with the cyclic carbonate. Accordingly, any such blocked primary amine group is referred to herein, and in the claims, as a "precursor" of a hydroxyalkyl carbamate group.

The cyclic carbonates which are to be reacted with the amines may comprise any suitable cyclic carbonate, including bis-carbonates, which are reactive with one or more of the primary amine groups of a multi-functional amine. Generally, five-member ring organic carbonates are preferred as compared to six-member ring organic carbonates because the latter are relatively more expensive and difficult to prepare. Accordingly, a preferred cyclic carbonate utilizable in the present invention has the formula given for the first member in equation (1) above, and wherein $R_a$ and $R_b$ may be the same or different, and each may comprise H, or a $C_1$ to $C_8$ aliphatic, cycloaliphatic, aromatic or heterocyclic compound. Ethylene carbonate and propylene carbonate are readily commercially available and are preferred reactants.

As indicated above, the amines utilized in accordance with the present invention to react with one or more cyclic carbonates to provide hydroxyalkyl carbamate-containing amine groups may be any one of a large number of compounds and, generally, may comprise multi-functional amines containing straight chain or branched alkyl, cycloalkyl or alkyl aromatic moieties, most preferably $C_1$ to $C_{20}$ alkyl, cycloalkyl or alkyl aromatic moieties and such moieties containing, in addition to at least one carbon atom, one or more heteroatoms. Such moieties containing one or more heteroatoms include, for example, those containing ether groups, thio groups and organo-silicon moieties. General representation of preferred classes of amines are given by the following formulas:

(a) 

where each x is independently 2 to 6 and n is 0 to 4;

(b) 

where $R_3$ is a $C_1$ to $C_{20}$ alkyl, cycloalkyl or alkyl aromatic moiety, and y is 2 or 3; and

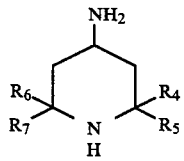

(c)

where each of $R_4$ and $R_6$ is independently H or a $C_1$ to $C_4$ organic moiety and each of $R_5$ and $R_7$ is independently a $C_1$ to $C_4$ alkyl moiety.

Suitable amines include the following fatty acid diamines of the general formula $RNHCH_2CH_2CH_2NH_2$ wherein R is a $C_1$ to $C_{20}$ organic moiety, e.g., hydrogenated tallow diamine, tall oil diamine, coco diamine, oleyl diamine and the like; ether diamines of the general formula $R'OCH_2CH_2CH_2NHCH_2CH_2CH_2NH_2$, wherein R' is a $C_1$-$C_{15}$ organic moiety; and silyl amines of the general formula $(C_2H_5O)_3SiCH_2CH_2CH_2NHCH_2CH_2CH_2NH_2$.

Preferred multi-functional amines for reacting with the cyclic carbonate include, for example, diethylene triamine and triethylene tetramine and preferred hydroxyalkyl carbamate compounds are diethylenetriamine bishydroxyethyl carbamate and triethylenetetramine bishydroxypropyl carbamate. It will be appreciated that those skilled in the art will, when utilizing polyamines, select conditions and reactants so as to avoid gellation in forming the polymer.

Reaction of a cyclic carbonate with the primary amine groups of one or more amines as indicated above will provide amines containing at least one hydroxyalkyl carbamate group in addition to unreacted secondary amines. Thus, amine-pendant hydroxyalkyl carbamate resins are obtained having structures in which one or more of the —NH$_2$ groups of the above formulas are converted to

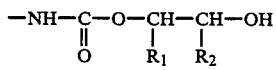

wherein each R$_1$ and R$_2$ independently H, or a C$_1$ to C$_{20}$ alkyl, cycloalkyl or alkyl aromatic moiety or such moieties containing heteroatoms as described above.

For example, a hydroxyalkyl carbamate group-containing amine found to be useful preparing hydrophilic polymers in accordance with the invention is obtained by reacting N,N-bis(6-aminohexyl)-2-[(6-aminohexyl)amino]butanediamide with propylene carbonate and has the formula:

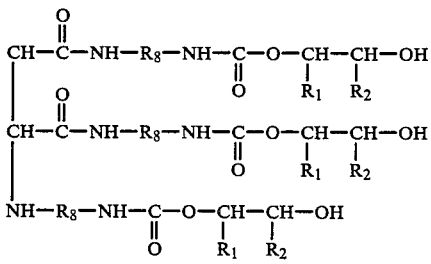

wherein each of R$_1$ and R$_2$ is as defined above and each R$_8$ is C$_6$ alkylene. Other useful amines of this type may be prepared wherein R$_8$ is independently a C$_2$ to C$_6$ alkylene moiety.

The epoxide material utilized in accordance with the invention may be a monomeric or polymeric epoxy containing material, preferably a resinous polyepoxide material containing two or more epoxy groups per molecule.

Among the known epoxides which have been found useful in the practice of the present invention are polyglycidyl ethers of polyphenols such as bisphenol-A or, generally, the reaction product of epichlorohydrin with a polyhydric phenol. As used herein, "polyhydric phenol" means and includes compounds such as bisphenol-A, bisphenol-F and bisphenol-S.

Polyepoxides made from polyhydric phenol resins such as novolac resins or the like comprise one suitable class of compounds. Polyglycidyl esters of polycarboxylic acids, such as the reaction products of epichlorohydrin or other similar epoxy compounds with reactants such as cyanuric acid, terephthalic acid, glucaric acid, succinic acid, oxalic acid and the like may also be employed.

Multi-functional amines as described above may be reacted with, for example, a polyepoxide of one of the following formulas:

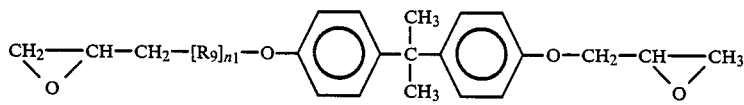

where R$_9$ is the repeating fragment

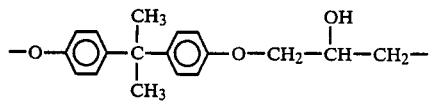

and n$_1$ is from 0 to 2;

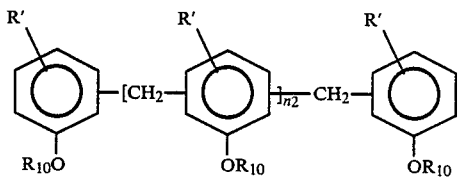

where R' is a hydrogen or a methyl group and R$_{10}$ is a hydrogen atom or a glycidyl group and n$_2$ is from 0 to 12;

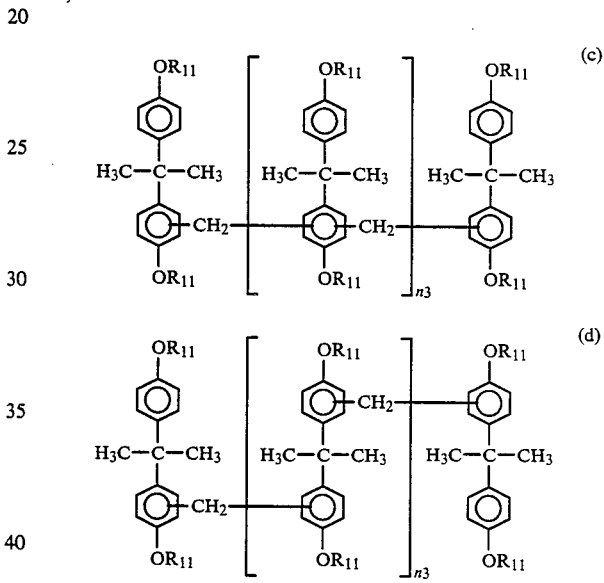

wherein, in (c) and (d), n$_3$ is independently 0 to 4, and R$_{11}$ is a hydrogen atom or a glycidyl group. In the claims, epoxides of the formula (c) or formula (d), or mixture thereof, are referred to as "aromatic novalac bisphenol-A resin". The defined term thus includes epoxides selected from the formula (c), or the formula (d), or combinations thereof.

Polyepoxides which are most preferred for the production of high performance coatings are the aromatic bisphenol-A and novalac types. Generally, it is preferred that on average a high number of hydroxyalkyl carbamate groups per molecule be present after reaction of the epoxides with the hydroxyalkyl carbamate-containing-amine or -polyamine compounds. At least two, but preferably three or more, hydroxyalkyl carbamate groups per molecule should be present as these groups impart water solubility/reducibility and are involved in cross-linking.

A suitable polyepoxide as described above is reacted with approximately one equivalent of the above described amines containing one or more secondary amine groups. The equivalent ratio of amine to epoxy groups should be approximately one to one. Ideally, all reactive epoxy groups will react with a secondary amine group to attach the amine to the epoxide and provide a substantially epoxy-free polymer.

In an alternative method of preparing the polymer of the invention, the epoxides are reacted with amines which contain, in addition to one or more secondary amine groups, ketimine groups in lieu of some or all of the above described hydroxyalkyl carbamate groups. After reaction of the secondary amine groups with the epoxy groups as described above, so that the amine groups are pendant upon the backbone epoxy polymer, the ketimine groups are hydrolyzed to form free amine groups and one or more suitable cyclic carbonates may then be added to the mixture to react with the resultant free amine groups. Thus, the multi-functional amine utilized to form the hydroxyalkyl carbamate will contain either an amine group reactable with a cyclic carbonate or a ketimine group convertible to an amine group reactable with the cyclic carbonate.

The water borne coating compositions of this invention are prepared by adding water, and, optionally, a catalyst and/or a cosolvent to the polymers of the invention. Depending upon the specific hydoxyalkyl carbamate-containing polymer and amount of cosolvent utilized, the polymers may vary in solubility from completely water soluble to water reducible. Even with the least water reducible resins it is often possible to obtain solids contents as low as 10 to 20% as clear solutions with only 20 to 30% cosolvents. Futhermore, these cosolvents may be the so called "environmentally exempt" solvents such as alcohols and glycols. Coating compositions with high solids contents (60 to 90%) with workable viscosities are attainable in many cases with no cosolvents.

A catalyst may be incorporated into the composition of the invention, either as an external catalyst or as an internal catalyst by incorporation within the polymer backbone during preparation, as is known in the art. While any suitable cross-linking catalyst may be utilized (such as known tin, zinc, and titanium compounds) ternary or quaternary compounds as described below are preferred and are utilized in order to attain the low temperature curing benefits of the invention. However, for example, dibutyltindilaurate or other tin or zinc catalysts are also useful as a cross-linking catalyst for the polymers of the invention.

Generally, the ternary or quaternary catalysts are known compounds of the formula:

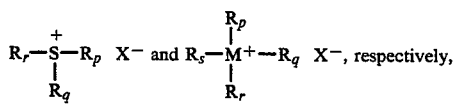

where $R_p$, $R_q$, $R_r$ and $R_s$ may be equivalent or different and may be $C_1$ to $C_{20}$ aliphatic, aromatic, benzylic, cyclic aliphatic and the like, where M may be nitrogen, phosphorous or arsenic (to provide, respectively, quaternary ammonium, phosphonium or arsonium compounds), where S is sulfur (to provide a ternary sulfonium compound) and where $X^-$ may be hydroxide, alkoxide, bicarbonate, carbonate, formate, acetate, lactate, and other carboxylates derived from volatile organic carboxylic acids or the like. Such salts of carboxylic acids are effective to promote the low temperature cure provided that the carboxylic acids are volatile. The ternary or quaternary catalysts are preferably water soluble or water reducible compounds.

In preparing coating compositions in accordance with the invention, the hydrophilic polymer is dissolved or dispersed in an aqueous medium which optionally may contain a suitable organic cosolvent, and, when an external catalyst is utilized, a catalyst such as dibutyltindilaurate or a quaternary ammonium compound is added. Generally, the external quaternary or ternary catalysts are selected so that they are water soluble or dispersible. Typically, not more than up to about 20 to 40% of the composition, sometimes less than 10%, comprises organic cosolvents. Strong bases such as alkali metal hydroxides (KOH, NaOH, LiOH, etc.) may also be included as catalysts in the composition.

The efficacy of the invention is demonstrated by the following examples of specific preferred embodiments thereof. Examples 1-3 illustrate the preparation of carbamate group-containing amines.

EXAMPLE 1

Diethylenetriamine in the amount of 206 grams (2 moles) and 600 grams of solvent methanol were added to a suitable reactor. 612 grams (6 moles) of propylene carbonate, which amount comprises 2 moles in excess of the stoichometric amount, was slowly added to the reactor under a nitrogen blanket while the temperature of the reactants was maintained at 15° to 20° C. by ice bath cooling. After complete addition, the mixture was stirred 8 hours at room temperature. Methanol was then removed by use of water pump vacuum and with steam bath heating. The resulting product solution comprised diethylenetriamine bishydroxypropyl carbamate and was 73% solids in propylene carbonate (theory 75% solids), had 2.16 meq/g secondary amine (theory 2.37 meq/g at 73% solids), and gave characteristic bands in the infrared for the hydroxypropyl carbamate groups.

EXAMPLE 2

To a suitable reactor containing 103 grams (1 mole) of diethylenetriamine and 300 grams of solvent methanol under a nitrogen atmosphere 184.8 grams (2.1 moles) of ethylene carbonate was slowly added. The temperature was maintained at 15° to 20° C. by ice bath cooling. After complete addition, the mixture was stirred at room temperature overnight. Methanol was then removed by use of a water pump vacuum and with steam bath heating. The resulting product solidified to a mass of white crystals upon cooling, mp 82° to 88° C. Recrystallization from ethanol afforded a pure product, mp 96° to 97° C., in nearly quantitative yield. The product gave completely consistant IR and NMR spectra for the bis-hydroxyethyl carbamate of diethylenetriamine, i.e., diethylenetriamine bis-hydroxyethyl carbamate.

EXAMPLE 3

To a suitable reactor containing 408 grams (4 moles) of propylene carbonate and 300 grams of solvent methanol, 292 grams (2 moles) of triethylenetetramine was slowly added while maintaining the temperature at 15° to 30° C. by bath cooling. Upon complete addition, the mixture was heated to 80° C. for approximately 3 hours after which only a trace band in the infrared could be seen for propylene carbonate. Solvent methanol was then removed by distillation, the last traces being removed at 5 mm of pressure with steam bath heating. On standing at room temperature, the product, which comprises triethylenetetramine bishydroxypropyl carbamate, solidified to a low melting paste. The product was found to be 98% nonvolatile and titrated in water (phenol red indicator) as though only one amine group per molecule titrated, showing an equivalent weight of 367 (theoretical molecular weight corrected to 98% solids in 357). Potentiometric titration with $HClO_4$ in acetic acid yielded an equivalent weight of 210 which is closer to theory. The infrared spectrum was completely consistent with structure and no problems were subsequently encountered using a theoretical equivalent weight of 175.

The following examples illustrate the preparation of specific water-based coating compositions in accordance with the present invention.

EXAMPLE 4

A. A self-cross-linking bisphenol-A hydroxypropyl carbamate-containing resin which can be reduced with water to at least 15% solids as a clear solution with only 20% by total composition weight of cosolvents was prepared from the following ingredients:

|  | Parts by Weight | Equivalents | Solids |
| --- | --- | --- | --- |
| EPON 828* | 150.9 | 0.82 | 150.9 |
| Carbamate-containing Amine of Example 1 | 380.0 | 0.82 | 277.4 |

*Shell Chemical Co. reaction product of epichlorohydrin and BP-A

The EPON 828 and the carbamate-containing amine of Example 1 were added to a suitable reactor under nitrogen equipped with a Cowels high speed stirrer. Upon stirring, the temperature was allowed to reach 100° C. (heat of exotherm) and was then maintained at this temperature by external cooling for one hour. After this, the mixture was stirred and heated at 70° C. for 4 hours more. The final product had a solids content of 80%.

B. A sprayable aqueous composition was made up by mixing 191.4 parts of the resin obtained in part A of this Example with 191.4 parts of deionized water and 15.3 parts of ethylene glycol monobutyl ether cosolvent. The resulting clear solution contained only 13.5% by total weight organic cosolvents and was 38.5% solids. To this solution was added 14.5 parts of aqueous 1 Molar tetrabutyl ammonium hydroxide catalyst and the contents were well stirred. This composition was applied, by spraying, to aluminum panels. The panels were baked at 250° F. (121° C.) for 20 minutes and showed film thickness of 0.3 to 0.4 mil after cure. The coatings were smooth, glossy, had 4H pencil hardness, passed 40 in-lb reverse impact, and resisted greater than 300 water and methyl ethyl ketone (MEK) double rubs.

EXAMPLE 4A

Example 4 was repeated, except that 29 parts of the catalyst (equivalent to 5% by weight solid catalyst on a solid catalyst to resin solids basis) was added. Resulting films cured at 220° F. (104.4° C.) for 20 minutes showed properties similar to those of the cured films of Example 4. Resulting films cured at 212° F. (100° C.) resisted over 200 water rubs but only 100 MEK rubs. Based on the foregoing, it appears that a somewhat longer cure time at temperatures as low as 200° F. (93.3° C.) would provide satisfactory film properties with properly catalyzed polymers of the invention.

EXAMPLE 5

A. A self-cross-linking novalac hydroxypropyl carbamate resin which can be reduced with water to at least 12% solids as a clear solution with 20% by total weight of cosolvent was prepared from the following ingredients:

|  | Parts by Weight | Equivalents | Solids |
| --- | --- | --- | --- |
| EPN 1139* | 128.3 | 0.75 | 128.3 |
| Carbamate-containing Amine of Example 1 | 347.3 | 0.75 | 253.5 |

*Ciba Geigy Co. reaction product of phenol-formaldehyde condensate with epichlorohydrin The EPN 1139 and carbamate-containing amine of Example 1 were reacted in the same manner as described in Example 4, controlling the exotherm by external cooling when necessary. The final product had a solids content of 80%.

B. A sprayable aqueous composition was prepared by dissolving 100 parts of the novolac-hydroxypropyl carbamate-containing resin of part A of this Example in 100 parts of deionized water and 15.4 parts of 1 Molar tetrabutyl ammonium hydroxide catalyst. The resulting clear solution contained only 9% organic solvent and was 39% solids. Aluminum panels were sprayed and then baked at 250° F. for 20 minutes. The resulting cured coatings were 0.5–0.6 mil thick, had 4H pencil hardness, passed 40 in-lb reverse impact, were smooth and glossy, and resisted greater than 300 MEK and water double rubs.

EXAMPLE 6

A. A self-cross-linking bisphenol-A hydroxyethyl carbamate-containing resin which can be reduced with water to at least 10% solids as a clear solution with 20% by total weight of cosolvent was prepared from the following ingredients:

|  | Parts by Weight | Equivalents | Solids |
| --- | --- | --- | --- |
| EPON 828 | 85.7 | 0.466 | 85.7 |
| Carbamate-containing-Amine of Example 2 | 130.0 | 0.466 | 130.0 |
| Butyl Cellosolve* | 53.9 | — | 0.0 |

*Monobutyl ether of ethylene glycol

The EPON 828, carbamate-containing amine of Example 2, and butyl Cellosolve were mixed and reacted as in Example 4. The final products had a solids content of 80%.

B. A composition for spray application was prepared by dissolving 100 parts of the BP-A hydroxyethyl carbamate of part A of this Example in 100 parts of deionized water and 7.7 parts of 1 Molar tetrabutyl ammonium hydroxide catalyst. The resulting clear solution contained only 10% organic cosolvent and was 39% solids. After spraying aluminum panels and then baking at 250° F. for 20 minutes, the film thicknesses were 0.3–0.4 mil. The coatings were smooth and glossy, had 4H pencil hardness, passed 40 in-lb reverse impact, and resisted greater than 300 MEK and water double rubs.

EXAMPLE 7

A. A self-cross-linking novolac hydroxyethyl carbamate-containing resin which can be reduced with water to 10% solids with only 10% by total weight cosolvent was prepared by replacing the EPON 828 in Example 6 with 79.7 parts of EPN 1139 and using 52.4 parts of butyl Cellosolve. After following the preparation procedure of Example 4, the resulting product was 80% solids.

B. A sprayable composition was prepared by dissolving 100 parts of the novalac hydroxyethyl carbamate-containing resin obtained in part A of this Example in 100 parts of deionized water and 15.4 parts of 1 Molar tetrabutyl ammonium hydroxide catalyst. The resulting clear solution contained only 9% organic cosolvent and was 39% solids. The composition was applied, by spraying, onto aluminum panels which were cured at 250° F. for 20 minutes. The resulting smooth, glossy coatings had 4H pencil hardness, were 0.3–0.4 mil thick, passed 40 in-lb reverse impact, and resisted greater than 300 MEK and water double rubs.

EXAMPLE 8

A. A self-cross-linking saturated hydroxyethyl carbamate-containing resin which can be reduced to at least 20% solids with 20% by total weight cosolvent was prepared from the following ingredients:

|  | Parts by Weight | Equivalents | Solids |
| --- | --- | --- | --- |
| EPONEX DRH 151* | 100.0 | 0.42 | 100.0 |
| Carbamate-containing Amine of Example 2 | 112.0 | 0.40 | 112.0 |

*Eponex DRH 151 - Shell Chemical Co. Hydrogenated BP-A epichlorohydrin product

The Eponex DRH 151 and carbamate-containing-amine of Example 2 were reacted in the same manner as described in Example 4, carefully controlling the exotherm with external cooling when necessary. The final product was 100% solids. This product was reduced to 80% solids with ethylene glycol monobutyl ether.

B. A sprayable composition was prepared by mixing 100 parts of the saturated epoxy-hydroxyethyl carbamate of Part A with 100 parts of deionized water and 15.4 parts of 1 Molar tetrabutyl ammonium hydroxide catalyst. The resulting clear solution at 39% solids and containing 9% organic cosolvents was sprayed onto aluminum panels. The panels were cured at 270° F. for 20 minutes and afforded film thicknesses of 0.4 to 0.5 mil. The coatings were smooth, glossy, had 3H pencil hardness, passed 40 in-lb reverse impact and resisted greater than 200 MEK rubs and 300 water rubs.

EXAMPLE 9

A. A more polymeric self-cross-linking BP-A hydroxypropyl carbamate-containing resin, water reducible to at least 35% solids with 25% cosolvent, was prepared from the following ingredients:

|  | Parts by Weight | Equivalents | Solids |
| --- | --- | --- | --- |
| EPON 828 | 110.4 | 0.6 | 110.4 |
| Carbamate-containing Amine of Example 3 | 35.7 | 0.2 | 35.0 |
| Carbamate-containing Amine of Example 1 | 185.2 | 0.4 | 135.2 |
| Butyl Cellosolve | 19.5 | — | — |

The EPON 828, the carbamate-containing amines of Example 1 and Example 3 and the butyl Cellosolve were mixed and reacted in the same manner as described in Example 4. The final very viscous product was 80% solids.

B. A sprayable composition was prepared by mixing 100 parts of the polymeric BP-A hydroxypropyl carbamate product of part A with 100 parts of 140° F. deionized water until a milky suspension was obtained. The stirred suspension was cooled to room temperature and 30 parts of butyl Cellosolve followed by 9.3 parts of tetrabutyl ammonium hydroxide catalyst was added. The resulting clear solution was 34% solids and contained 25% organic cosolvents. This composition was applied, by spraying, onto aluminum panels which were then cured at 250° F. for 20 minutes. The cured coatings were 0.4 to 0.5 mil thick, were smooth and glossy, had 4H pencil hardness, passed 40 in-lb reverse impact, and resisted greater than 300 MEK and water double rubs.

EXAMPLE 10

Example 4 was repeated in all essential details, except that in place of the tetrabutyl ammonium hydroxide an equivalent amount of benzyltrimethyl ammonium hydroxide was substituted as catalyst. The cured coatings were similar in all film properties tested.

EXAMPLE 11

Example 4 was repeated in all essential details except that in place of the tetrabutyl ammonium hydroxide an equivalent amount of tetramethyl ammonium acetate was substituted as catalyst. Some precipitate formed and solution was re-effected by adjusting the solids to 30% with ethylene glycol monobutyl ether. After spraying and curing panels at 250° F., the coatings had similar film properties as those obtained in Example 4.

Examples 4–7 and 9–11 show that utilization of a quaternary ammonium catalyst provides water based coatings which can be cured at low temperature, e.g., 250° F. (121° C.). Temperatures as low as 200° F. (93° C.) can successfully be utilized when an appropriate amount of quaternary catalyst is employed. Generally, the amount of quaternary catalyst employed to effectuate a low temperature cure is about 0.1 to 10%, preferably 1 to 5%, by weight of the weight of resin solids.

The following Example 12 shows that use of a non-quaternary compound catalyst requires a much higher temperature cure, in excess of 300° F. (149° C.), to obtain a satisfactory coating.

EXAMPLE 12

Example 4 was repeated in all essential details except that in place of the tetrabutyl ammonium hydroxide catalyst an equivalent amount of dibutyltindilaurate (a common commercially utilized urethane catalyst) was substituted as catalyst. The dibutyltindilaurate catalyst was not fully compatible with the water based system but for the short term formed a relatively stable suspension. Cure was not effected at 250° F. after 20 minutes and in fact 330° to 350° F. for 20 minutes was necessary. Furthermore, the coatings cured at 350° F. were poor in appearance and very brittle.

The polymers of the invention, while having the great advantage from the point of view of environmental and safety considerations of being water soluble/reducible, can also be employed with organic solvents, as shown in Example 13.

EXAMPLE 13

All essential details of Examples 4, 5, 6 and 7 were repeated, except that butyl Cellosolve was substituted in place of all the water solvent and the aqueous tetrabutyl ammonium hydroxide catalyst was replaced by an equivalent amount of methanolic benzyltrimethyl ammonium hydroxide. When baked at 250° F. for 20 minutes the films from all of these nonaqueous compositions were similar in properties to those obtained from the aqueous systems.

Generally, a wide class of epoxides is suitable for reaction with amines containing hydroxyalkyl carbamate groups (or precursors thereof) to provide the polymers of the invention. However, in order to maintain good water solubility/reducibility it is important to select backbone polymers that are of low molecular (equivalent) weight for monofunctional epoxides or of low equivalent weight for di- or polyfunctional epoxides. For high performance coatings, di- or polyfunctional epoxides are preferred, such as the classes of compounds described above. The use of such di- or polyfunctional epoxides allows for a high proportion of hydroxyalkyl carbamate groups to be incorporated into the epoxide, thereby providing a hydrophilic resin, i.e., one which is soluble or reducible in water. In addition to the epoxides described above, resins of the following formulas have been found to be well suited to the practice of the present invention:

(a) tris (hydroxphenyl) methane based resins of the formula:

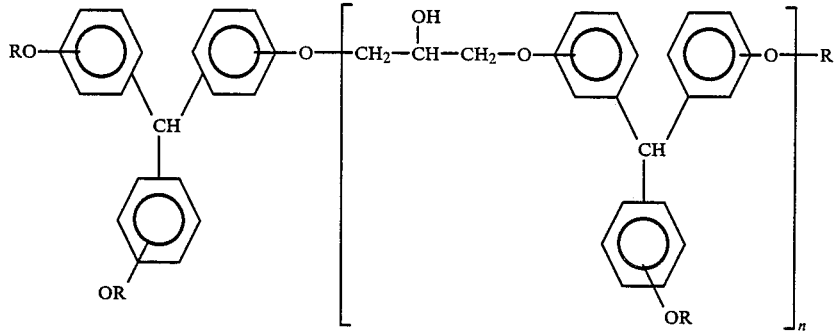

wherein,

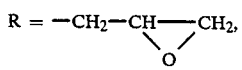

n is 0 to about 5 and preferably about 0 to about 0.7, on average; and (b) triglycidyl isocyanurate polyepoxy resins of the general formula:

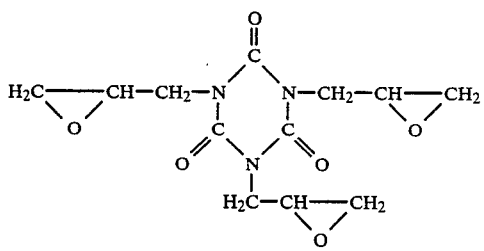

As used herein and in the claims, "tris (hydroxyphenyl) methane based resin" means a resin of formula (a) above wherein n is 0 to 5, and "triglycidyl isocyanurate polyepoxy resin" means a resin of formula (b) above.

The following Example 14 shows the preparation of a resin in accordance with the invention, which resin is completely water soluble.

EXAMPLE 14

A. An isocyanurate hydroxypropyl carbamate-containing resin was prepared from the following ingredients:

|  | Parts by Weight | Equivalents | Solids |
| --- | --- | --- | --- |
| ARALDITE PT 810* | 125.4 | 1.0 | 125.4 |
| Carbamate-containing Amine of Example 1 | 463.1 | 1.0 | 338.1 |

*Ciba Geigy Co. reaction product of isocyanuric acid with epichlorohydrin

B. The ARALDITE PT 810 and the carbamate-containing amine of Example 1 were added to a suitable reactor under nitrogen equipped with a Cowels high speed stirrer. Upon heating to 80° C. the suspension of reactants began to exotherm mildly and the temperature reached 113° C. for 4 hours. The final product had a solids content of 79%.

C. A sprayable aqueous composition was prepared by dissolving 50.0 parts of the isocyanurate hydroxypropyl carbamate-containing resin of part B of this Example in 207.3 parts of deionized water, followed by adding 6.0 parts of ethylene glycol monobutyl ether and 8.5 parts of diethylene glycol monobutyl ether flow-promoting solvents. This solution which contains a total of only 9.2% organic solvents by weight, was filtered and 4.9 parts of 40% aqueous tetrabutyl ammonium hydroxide catalyst was added. The resulting clear solution was 14.8% solids. This composition was applied by spraying onto aluminum panels. The coatings were cured at 250° F. for 60 minutes and afforded film thicknesses of 0.15 to 0.20 mil. The coatings were smooth, glossy, had 4H pencil hardness, passed 40 in-lb impact tests, and resisted greater than 300 MEK rubs and 200 water rubs.

As mentioned above, utilization of a suitable ternary or quaternary ammonium catalyst provides a coating which can be cured at low temperature, e.g., 250° F. (121° C.). Temperatures as low as 200° F. (93° C.) can successfully be utilized when an appropriate amount of such catalyst is employed. The amount of such catalyst employed to effectuate a low temperature cure is generally about 0.1 to 10%, preferably 1 to 5%, by weight of the weight of resin solids.

Generally, reference herein and in the claims to hydroxyalkyl carbamates and compounds containing the same, including structural formulas of the same, is intended to include the various isomeric species thereof, if any.

While the invention has been described with respect to specific preferred embodiments, it will be apparent to one skilled in the art that numerous variations may be made to the embodiments without departing from the spirit and scope of the invention.

What is claimed is:

1. A hydrophilic, substantially epoxy-free self-cross-linkable polymer containing hydroxyalkyl carbamate groups and one or more tertiary amine groups per molecule.

2. The polymer of claim 1 obtained as the reaction product of (a) an epoxy resin having an average epoxy equivalent weight of from about 100 to about 700 and (b) one or more amines having at least one secondary amine group and at least one hydroxyalkyl carbamate group or precursor thereof.

3. The polymer of claim 2 wherein said amines containing hydroxyalkyl carbamate groups are obtained by reaction of an amine with a cyclic carbonate.

4. The polymer of claim 2 wherein said epoxy is selected from the group consisting of: (i) the reaction product of epichlorohydrin and a polyhydric phenol, and (ii) the reaction product of epichlorohydrin and a condensation product of phenol with acetone and formaldehyde.

5. The polymer of claim 1 containing from about 3.5 to about 5.7 meq hydroxyalkyl carbamate per gram of resin solids.

6. The polymer of claim 1 containing from about 4.2 to about 5.4 meq hydroxyalkyl carbamate per gram of resin solids.

7. The polymer of claim 2 wherein said epoxy resin has an epoxy equivalent weight of from about 100 to about 300.

8. A hydrophilic, substantially epoxy-free polymer which is self-cross-linkable through urethane groups comprising a hydroxyalkyl carbamate-containing resin having more than one tertiary amine group and more than two hydroxyalkyl carbamate groups per molecule, said polymer containing from about 3.5 to about 5.7 meq hydroxyalkyl carbamate per gram of resin solids and being obtained by reaction of epoxy groups of one or more epoxides with a secondary amine group of one or more amines containing hydroxyalkyl carbamate groups or precursors thereof, said epoxide having an average epoxy equivalent weight of from about 100 to about 700.

9. The polymer of claim 8 wherein said epoxide is selected from the group consisting of (i) the reaction product of epichlorohydrin and polyhydric phenol, and (ii) the reaction product of epichlorohydrin and the condensation product of phenol with acetone and formaldehyde.

10. The polymer of claim 8 wherein said amines are selected from the group consisting of:

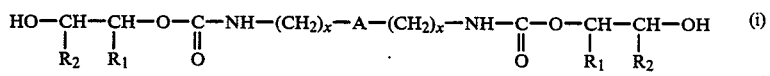

wherein A is [NH(CH$_2$)$_x$]$_n$NH; n is 0 to 10; each x is independently 2 to 6; each of R$_1$ and R$_2$ is independently H, or a C$_1$ to C$_{20}$ alkyl, cycloalkyl or alkylaromatic moiety or any of the foregoing containing one or more heteroatoms in addition to at least one carbon atom;

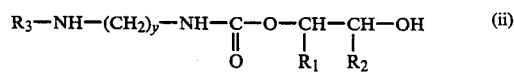

wherein: y is 2 or 3; and each of R$_1$ and R$_2$ is as defined above and R$_3$ is a C$_1$ to C$_{20}$ alkyl, cycloalkyl or alkyl aromatic moiety;

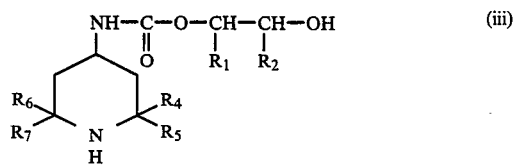

wherein: each of R$_4$ and R$_6$ is independently H or C$_1$ to C$_4$ alkyl moieties and each of R$_5$ and R$_7$ is independently a C$_1$ to C$_4$ alkyl moiety or such moiety containing one or more heteroatoms in addition to at least one carbon atom; and

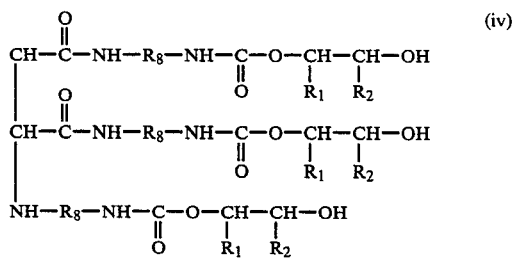

wherein each of R$_1$ and R$_2$ is as defined above and each R$_8$ is independently a C$_2$ to C$_6$ alkylene moiety; and said polymer contains from about 3.5 to about 5.7 meq hydroxyalkyl carbamate per gram of resin solids.

11. The polymer of claim 8 wherein said epoxide is selected from the group consisting of the following polyepoxides:

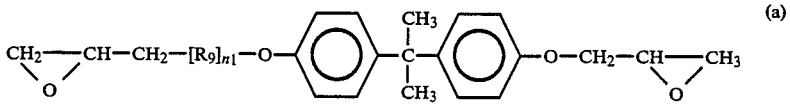
(a)

where $R_9$ is the repeating fragment

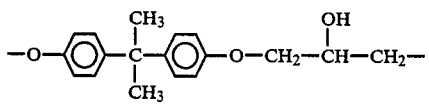

and $n_1$ is from 0 to 2;

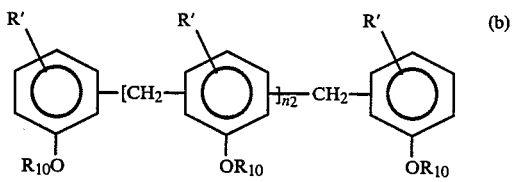
(b)

where R' is a hydrogen or a methyl group and $R_{10}$ is a hydrogen atom or a glycidyl group and $n_2$ is from 0 to 12;
(c) an aromatic novalac bisphenol-A resin;
(d) a tris (hydroxyphenyl) methane based resin; and
(e) a triglycidyl isocyanurate resin.

12. A method of preparing a hydrophilic self-cross-linkable polymer comprising reacting (a) an epoxide having an average epoxy equivalent weight of from about 100 to about 700, with (b) an amine containing at least one secondary amine group and at least one group selected from the class consisting of hydrolyzable blocked primary amine groups and hydroxyalkyl carbamate groups, to form a substantially epoxy-free material and, when said blocked primary amine groups are present, hydrolyzing the same to unblock said primary amine groups and then reacting a cyclic carbonate with said primary amine groups to form said hydroxyalkyl carbamate groups; the reactants (a) and (b) being selected to form said polymer with from about 3.5 to about 5.7 meq hydroxyalkyl carbamate per gram of resin solids.

13. The method of claim 12 wherein said epoxide has an average epoxy equivalent weight of from about 100 to about 300 and said polymer has from about 4.2 to about 5.4 meq hydroxyalkyl carbamate per gram of resin solids.

14. A coating composition comprising a hydrophilic, self-cross-linkable polymer containing hydroxyalkyl carbamate groups and one or more tertiary amine groups, in a liquid medium.

15. The composition of claim 14 wherein said liquid medium is an aqueous medium and said polymer is obtained as the reaction product of (a) an epoxy resin having an average epoxy equivalent weight of from about 100 to about 700 and (b) one or more amines having at least one secondary amine group which is reactive with an epoxy group of said epoxy resin and having at least one hydroxyalkyl carbamate group or precursor thereof.

16. The composition of claim 15 further including a cross-linking catalyst.

17. The composition of claim 14 wherein said medium is an aqueous medium.

18. The composition of claim 15 wherein said epoxy resin is selected from the class consisting of: (i) the reaction product of epichlorohydrin and a polyhydric phenol, and (ii) the reaction product of epichlorohydrin and a condensation product of phenol with acetone and formaldehyde.

19. The composition of claim 18 further including a quaternary ammonium catalyst.

20. A method of preparing a cross-linked coating from the composition of claim 16 comprising applying the composition onto a substrate and heating the coated substrate at a temperature and for a time sufficient to cure the applied coating.

21. The method of claim 20 wherein the catalyst is selected from the class consisting of one or more of quaternary ammonium, phosphonium and arsonium compounds and ternary sulfonium compounds.

22. The method of claim 20 wherein the catalyst is a quaternary ammonium compound.

23. The method of claim 21 wherein the coated substrate is heated to a temperature of from about 200° to about 250° F. (from about 93° to about 121° C.) to cure the applied coating.

24. The composition of claim 16 wherein said catalyst is selected from the class containing of quaternary and ternary compounds.

25. The composition of claim 16 wherein said cross-linking catalyst is a metal catalyst.

26. The composition of claim 25 wherein said metal catalyst is selected from the group consisting of tin, zinc and titanium compounds.

27. The composition of claim 16 wherein said catalyst is dibutyltindilaurate.

28. The polymer of claim 8 wherein said epoxide is the reaction product of hydrogenated bisphenol-A and epichlorohydrin.

29. The method of claim 12 wherein said epoxide is the reaction product of hydrogenated bisphenol-A and epichlorohydrin.

30. The composition of claim 15 wherein said epoxy resin is the reaction product of hydrogenated bisphenol-A and epichlorohydrin.

31. The polymer of claim 10 wherein $R_3$ contains one or more heteroatoms.

* * * * *